United States Patent
Saito et al.

(10) Patent No.: US 9,382,616 B2
(45) Date of Patent: Jul. 5, 2016

(54) CHEMICAL VAPOR DEPOSITION RAW MATERIAL COMPRISING ORGANOPLATINUM COMPOUND, AND CHEMICAL VAPOR DEPOSITION METHOD USING THE CHEMICAL VAPOR DEPOSITION RAW MATERIAL

(71) Applicant: TANAKA KIKINZOKU KOGYO K.K., Tokyo (JP)

(72) Inventors: Masayuki Saito, Ibaraki (JP); Kazuharu Suzuki, Ibaraki (JP); Toshiyuki Shigetomi, Ibaraki (JP); Shunichi Nabeya, Ibaraki (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 14/344,603

(22) PCT Filed: Oct. 12, 2012

(86) PCT No.: PCT/JP2012/076387
§ 371 (c)(1),
(2) Date: Mar. 12, 2014

(87) PCT Pub. No.: WO2013/054863
PCT Pub. Date: Apr. 18, 2013

(65) Prior Publication Data
US 2015/0030772 A1 Jan. 29, 2015

(30) Foreign Application Priority Data

Oct. 14, 2011 (JP) ................ P2011-226568

(51) Int. Cl.
| | | |
|---|---|---|
| *C23C 16/00* | (2006.01) | |
| *C23C 16/18* | (2006.01) | |
| *C07F 15/00* | (2006.01) | |
| *C23C 16/448* | (2006.01) | |
| *C23C 16/46* | (2006.01) | |

(52) U.S. Cl.
CPC .............. *C23C 16/18* (2013.01); *C07F 15/0086* (2013.01); *C23C 16/4485* (2013.01); *C23C 16/46* (2013.01)

(58) Field of Classification Search
CPC ....................................................... C23C 16/18
See application file for complete search history.

(56) References Cited

U.S. PATENT DOCUMENTS

| | | | |
|---|---|---|---|
| 5,783,716 A | 7/1998 | Baum et al. | |
| 5,929,267 A | 7/1999 | Kadokura | |
| 6,162,712 A | 12/2000 | Baum et al. | |

FOREIGN PATENT DOCUMENTS

| | | |
|---|---|---|
| JP | H08-157490 A | 6/1996 |
| JP | 11-292889 A | 10/1999 |
| JP | 2001-504159 A | 3/2001 |
| JP | 2008-231473 A | 10/2008 |

OTHER PUBLICATIONS

Shaver; Preparation of some cyclopentadienyl platinum(IV) complexes; Can. J. Chem. 56; pp. 2281-2285; 1978.*
Chemical Abstracts XP-002735246. Shaver, Alan; Preparation of some cyclopentadienylplatinum (IV) complexes. Canadian Journal of Chemistry; (1978); 56(17) 2281-5.
Dryden, Neil H., et al. Chemical Vapor Deposition of Platinum: New Precursors and Their Properties. Chemistry of Materials 3(1991)Jul./Aug. No. 4; 677-685.
EP12839806.2 Search Report.

* cited by examiner

*Primary Examiner* — Elizabeth Burkhart
(74) *Attorney, Agent, or Firm* — Roberts & Roberts, LLP

(57) ABSTRACT

A chemical vapor deposition raw material for producing a platinum thin film or a platinum compound thin film by a chemical vapor deposition method, wherein the chemical vapor deposition raw material includes an organoplatinum compound having cyclooctadiene and alkyl anions coordinated to divalent platinum, and the organoplatinum compound is represented by the following formula. Here, one in which $R_1$ and $R_2$ are any combination of propyl and methyl, propyl and ethyl, or ethyl and methyl is particularly preferred.

[Formula 1]

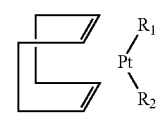

wherein $R_1$ and $R_2$ are alkyl groups, and $R_1$ and $R_2$ are different; and a number of carbon atoms of $R_1$ and $R_2$ is 3 to 5 in total.

4 Claims, No Drawings

CHEMICAL VAPOR DEPOSITION RAW MATERIAL COMPRISING ORGANOPLATINUM COMPOUND, AND CHEMICAL VAPOR DEPOSITION METHOD USING THE CHEMICAL VAPOR DEPOSITION RAW MATERIAL

BACKGROUND OF THE INVENTION

1. Field of the Invention

The present invention relates to a chemical vapor deposition raw material comprising an organoplatinum compound for producing a platinum thin film or a platinum compound thin film by a chemical vapor deposition method, the CVD method or the ALD method. The present invention particularly relates to a chemical vapor deposition raw material that can form a platinum thin film even at a low temperature of 300° C. or lower while having moderate stability.

2. Description of the Related Art

As an electrode material for a field effect transistor (FET) incorporated into an integrated circuit, a steric Ni—Pt silicide electrode having a three-dimensional structure is known. In the production of this Ni—Pt silicide electrode, it is required that when a Pt thin film and a Ni thin film are formed on preliminarily produced Si having a steric structure, the Si is uniformly covered with the Pt thin film and Ni thin film electrodes in the same proportion along the steric shape. It is assumed that in order to produce such a platinum thin film, the use of a chemical vapor deposition method, such as the CVD method, which provides excellent step coverage, is essential. Also for the gate electrode of an FET, a chemical vapor deposition method, such as the CVD method, which enables film formation at low temperature, is preferred in size reduction and performance enhancement.

As raw materials for producing platinum thin films or platinum compound thin films by the CVD method, many compounds have been conventionally known. Examples thereof include a bis(acetylacetonato)platinum(II) complex (Patent Literature 1), a cyclopentadienyltrimethylplatinum (IV) complex (Patent Literature 2), and a tetrakis(trifluorophosphine)platinum compound (Patent Literature 3). Generally, examples of the required performance of these CVD raw materials include high vapor pressure, and capability of film formation at low temperature due to low decomposition temperature. In addition, in view of handling properties, they are preferably in a liquid state at ordinary temperature.

At such requirements, in order to provide a CVD raw material having higher vapor pressure, a compound in which cyclooctadienyl in which at least one hydrogen atom is replaced by an alkyl group, and alkyl anions having 2 to 4 carbon atoms are coordinated to a platinum atom is provided (Patent Literature 4). As described in Patent Literature 4, when an alkyl group is introduced into cyclooctadienyl that is a ligand, the vapor pressure of the platinum complex decreases due to an increase in molecular weight, thereby providing properties not preferred as a CVD raw material compound. But, in Patent Literature 4, it is described that by the introduction of an alkyl group into cyclooctadienyl, the thermal stability of the platinum complex is improved, and decomposition at the stage of heating and vaporizing the compound can be suppressed.

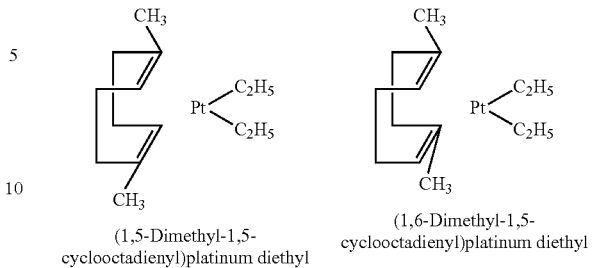

(1,5-Dimethyl-1,5-cyclooctadienyl)platinum diethyl (1,6-Dimethyl-1,5-cyclooctadienyl)platinum diethyl

PRIOR ART LITERATURE

Patent Literature

[Patent Literature 1] National Publication of International Patent Application No. 2001-504159
[Patent Literature 2] Japanese Patent Application Laid-Open No. 11-292889
[Patent Literature 3] Japanese Patent Application Laid-Open No. 2008-231473
[Patent Literature 4] Japanese Patent Application Laid-Open No. 8-157490

SUMMARY OF THE INVENTION

Problem to be Solved by the Invention

In the chemical vapor deposition raw materials comprising the conventional organoplatinum compounds described above, some of the properties required of CVD compounds can be enhanced, but they do not have all the other required properties in good balance. For example, in the platinum compound in Patent Literature 4 having improved thermal stability, pyrolysis at the stage of vaporizing the platinum compound can be suppressed because the thermal stability is improved. But, because of its high stability, at the stage of forming a film of platinum, the decomposition reaction of the platinum compound does not proceed easily, and it has been difficult to stably form a pure platinum thin film containing no impurities.

Based on such a background, the present invention provides a chemical vapor deposition raw material comprising a platinum compound that has the properties required of a CVD compound in a well-balanced manner. In other words, the present invention provides a chemical vapor deposition raw material that has high vapor pressure, is capable of film formation at low temperature, and allows easy film formation on a steric structure, and additionally that is not pyrolyzed at a vaporization stage, and can decompose easily at a film formation stage to form a platinum thin film having high purity.

Means for Solving the Problem

The present invention that solves the above problem relates to a chemical vapor deposition raw material for producing a platinum thin film or a platinum compound thin film by a chemical vapor deposition method, wherein the chemical vapor deposition raw material comprises an organoplatinum compound having cyclooctadiene and alkyl anions coordinated to divalent platinum, the organoplatinum compound being represented by the following formula:

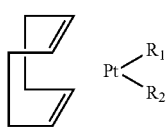

[Formula 2]

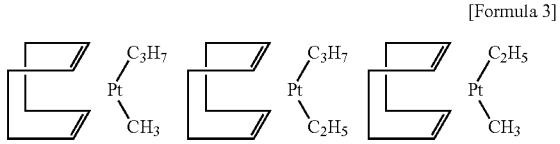

[Formula 3]

wherein $R_1$ and $R_2$ are alkyl groups, and $R_1$ and $R_2$ are different; and the number of carbon atoms of $R_1$ and $R_2$ is 3 to 5 in total.

The platinum compound according to the present invention is one in which cyclooctadiene and alkyl anions as ligands are coordinated to divalent platinum. The cyclooctadiene that is a ligand is known to be able to improve the thermal stability of a platinum complex by the introduction of an alkyl group, as described above. But, for the platinum compound of the present invention, one in which cyclooctadiene is not substituted by an alkyl group or the like is used. A complex in which cyclooctadiene not substituted by an alkyl group is coordinated as in the present invention provides an advantage that the vapor pressure increases because the molecular weight of the complex decreases. Further, the molecular weight of the ligand itself liberated by the decomposition of the complex in film formation is also small, and therefore, the ligand evaporates easily thereby to decrease the risk that the ligand is mixed into the platinum thin film as an impurity. Therefore, a pure platinum thin film containing no impurities can be made.

On the other hand, a platinum compound in which an alkyl group is introduced into cyclooctadiene is preferred in that the thermal stability at the vaporizing stage can be improved in platinum thin film formation. However, because the platinum complex is too stabilized, pyrolysis does not occur easily at the stage of forming a film of platinum, and therefore, the heating temperature required for the film formation tends to increase. In addition, when the cyclooctadiene released from the platinum complex by pyrolysis during film formation has an alkyl group, the cyclooctadiene has a high boiling point due to an increase in molecular weight, and is difficult to evaporate from the film formation chamber after the pyrolysis, and the possibility of providing an impurity into the platinum thin film increases.

The alkyl anions $R_1$ and $R_2$ that are the other ligands are different from each other. Thus, the symmetry of the complex molecule decreases, and crystallization does not occur easily. In other words, a platinum compound in a liquid state having a low melting point is easily obtained. In addition, the number of carbon atoms of the alkyl anions $R_1$ and $R_2$ is 3 to 5 in total. Because of the moderate number of carbon atoms, it is possible to prevent a decrease in stability of the platinum complex, which occurs when the number of carbon atoms is large, and a decrease in vapor pressure accompanying an increase in the molecular weight of the platinum complex.

The combination of the alkyl anions $R_1$ and $R_2$ is preferably any of propyl and methyl, propyl and ethyl, or ethyl and methyl (Formula 3). Platinum compounds in which the alkyl anions of these combinations are coordinated have a low melting point, and are likely to be in a liquid state at ordinary temperature.

For the platinum that is the central metal for the above-described ligands, divalent or tetravalent platinum having a positive charge is known to be stable. In the present invention, in view of the handling properties of compounds in the processes of synthesis, purification, and storage, development has been promoted with divalent platinum complexes having moderate stability.

The organoplatinum compound according to the present invention is useful for platinum thin film formation by the CVD method or the ALD method. In this thin film formation method, a platinum complex that is a raw material compound is vaporized by heating in a vacuum to generate a raw material gas. This raw material gas is blown on a heated substrate surface to pyrolyze the complex to form a platinum thin film, and the compound described above is used as an organoplatinum compound.

The heating temperature for the film formation can be set to 150° C. to 500° C. Since setting the film formation temperature to the low temperature is one of the objects of the present invention, the heating temperature is preferably 150° C. to 350° C., more preferably 200 to 350° C. At lower than 150° C., the film formation reaction does not proceed easily, and the required film thickness is difficult to obtain. At too high temperature, it is difficult to form a uniform thin film on a steric electrode, and it also tends to be difficult to maintain the performance of an FET device.

The organoplatinum compound of the present invention described above can be produced by the reaction of a (1,5-cyclooctadienylalkylplatinum(II)) halide with an alkyl-lithium.

Effects of Invention

The chemical vapor deposition raw material according to the present invention comprising an organoplatinum compound has high vapor pressure, is capable of film formation at low temperature, allows easy film formation on a steric structure, and also has excellent stability and handling properties. Therefore, the chemical vapor deposition raw material according to the present invention is useful as a CVD raw material. Particularly, the chemical vapor deposition raw material according to the present invention is preferred as a steric Ni—Pt silicide electrode material having a three-dimensional structure.

DETAILED DESCRIPTION OF THE PREFERRED EMBODIMENTS

The best embodiment in the present invention will be described below.

Example 1

In this embodiment, 1,5-cyclooctadienylmethylpropyl-platinum(II) in which a methyl group and a propyl group were coordinated as alkyl anions (alkyl groups) that were ligands was produced. The reaction formula of the compound synthesis is as follows. The production process will be described below for each stage.

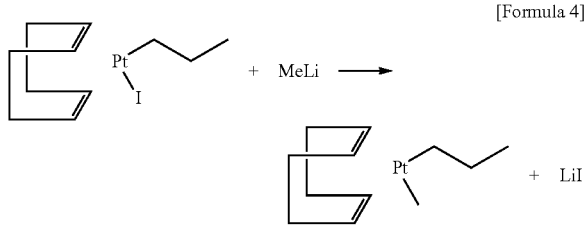

[Formula 4]

Into a flask in which an Ar atmosphere was provided, 4.73 g (0.01 mol) of (1,5-cyclooctadienylpropylplatinum(II)) iodide and 70 ml of dry diethyl ether were introduced. The obtained suspension was cooled to −20° C., and 7.5 ml of 1.6 mol/l methyllithium (0.012 mol, diethyl ether was used as a solvent) was dropped over 5 minutes. Stirring was continued overnight with a mechanical stirrer, and then, an aqueous solution (20 ml) of ammonium chloride (1.5 g) was dropped to stop the reaction. The black precipitate contained in the reaction solution was removed by suction filtration, and the diethyl ether, the solvent, was distilled off with an evaporator. The obtained crude product was a yellow liquid (3.30 g). The crude product was purified with column chromatography (filler: alumina, eluent: pentane) followed by recrystallization (solvent: pentane) at −80° C. to obtain 2.40 g (yield 66.4%) of the target compound (melting point: 5° C. or lower) that was a transparent liquid at room temperature.

Example 2

1,5-Cyclooctadienylethylpropylplatinum(II) in which a propyl group and an ethyl group were coordinated as alkyl anions (alkyl groups) was produced.

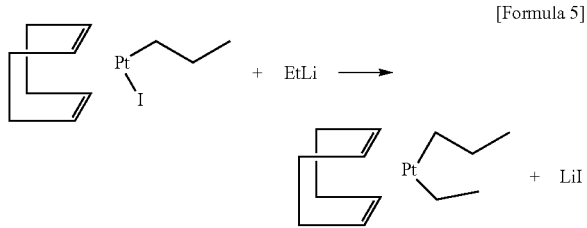

[Formula 5]

Into a flask in which an Ar atmosphere was provided, 4.73 g (0.01 mol) of (1,5-cyclooctadienylpropylplatinum(II)) iodide and 70 ml of dry diethyl ether were introduced. The obtained suspension was cooled to −20° C., and 24 ml of a 0.5 mol/l ethyllithium solution (0.012 mol, a mixed solvent of benzene and cyclohexane was used as a solvent, benzene: cyclohexane=9:1) was dropped over 15 minutes. Stirring was continued overnight with a mechanical stirrer, and then, an aqueous solution (20 ml) of ammonium chloride (1.5 g) was dropped to stop the reaction. The black precipitate contained in the reaction solution was removed by suction filtration, and the solvent was distilled off with an evaporator. The obtained crude product was a yellow liquid (3.74 g). The crude product was purified by column chromatography (filler: alumina, eluent: pentane) followed by recrystallization (solvent: pentane) at −80° C. to obtain 2.43 g (yield 64.7%) of the target compound (melting point: 23° C.) that was a transparent liquid at room temperature.

One of preferred conditions of the production processes described above is setting the reaction temperature to room temperature or lower, because at room temperature or lower, side reactions are suppressed thereby to allow the target compound with high yield to be obtained. In addition, the alkyllithium is preferably dropped, rather than being introduced in a large amount at a time; because if the alkyllithium is introduced in a large amount, a large amount of reaction heat is generated to raise the temperature of the reaction solution, which result in producing by-products different from the target compound. In addition, the amounts of the (1,5-cyclooctadienylalkylplatinum(II)) halide and the alkyllithium added are preferably in the range of 1:1 to 1:1.5 in terms of a molar ratio. In this range of the amounts added, the alkylation reaction is allowed to proceed sufficiently, and the production of side reaction products produced by the addition of an excess amount of the alkyllithium can be suppressed, which result in synthesis of the target complex with high yield.

Comparative Example (1,5-Dimethyl-1,5-cyclooctadienyl)platinum diethyl described in Reference 4 was produced. In 200 ml of water, 10 g of $K_2PtCl_4$ was dissolved, 100 ml of n-propyl alcohol was added thereto, and further 20 ml of 1,5-dimethyl-1,5-cyclooctadiene and 0.18 g of stannous chloride were added. This mixture was stirred for about 2 days, and then filtered. Acetone was added to the obtained solid, and the solid was suspended. To the suspended solution, 7.2 g of sodium iodide was added, and the mixture was stirred. Next, the acetone was distilled off under reduced pressure, and the residue was washed with water and then dried to obtain 8.5 g of (1,5-dimethyl-1,5-cyclooctadienyl)diiodoplatinum (1,5-DM-CODPtI$_2$). To the 1,5-DMCODPtI$_2$, 100 m of dry diethyl ether was added, 100 ml of an ethylmagnesium iodide ether solution (Grignard reagent) was added, and the mixture was stirred for 3 hours. While the mixture was cooled, a saturated aqueous solution of ammonium chloride was added thereto for hydrolysis followed by filtration. The filtrate was separated into an ether layer and an aqueous layer. The aqueous layer was extracted with 100 ml of diethyl ether, and the ether layer was combined followed by drying with anhydrous magnesium sulfate. The ether was distilled off under reduced pressure (30° C./2 torr) to obtain 2.3 g of a yellow liquid that was a compound.

Physical property evaluation (pyrolysis properties): For the compounds of Examples 1 and 2 and Comparative Example, pyrolysis properties were evaluated by TG-DTA. In the analysis, the weight change of the samples was observed when the platinum compounds were heated from 25° C. to 500° C. at a temperature increase rate of 3° C./min under an argon gas flow (200 mL/min). The temperatures at which the weight decrease of the compounds of Example 1 and Example 2 started were 124.5° C. and 120.1° C., respectively. The TG-DTA measurement results are shown in Table 1.

TABLE 1

|  | Weight decrease start temperature | Weight decrease end temperature | Residue weight |
|---|---|---|---|
| Example 1 | 125° C. | 177° C. | 46.37 wt % |
| Example 2 | 120° C. | 181° C. | 49.47 wt % |
| Comparative Example | 80° C. | 130° C. | 0.00 wt % |

The weight decrease of the compounds of Examples 1 and 2 observed by TG ended at 177° C. for Example 1 and at 181° C. for Example 2. The TG measurement was also subsequently continued to 500° C., but no weight decrease was observed at all. In addition, the weight of the residues remaining after the end of the measurement was 46.37% for Example 1 and 49.47% for Example 2, showing values close to the theoretical content of platinum contained in the compounds of Examples 1 and 2 (Example 1: 53.98%, Example 2: 51.96%). In addition, also from the fact that the residues are solids showing a white metallic luster, the residues can be presumed to be metal platinum produced by pyrolysis.

The TG-TDA measurement results are now summarized. It was found that the pyrolysis of the compounds of Examples 1 and 2 ended at low temperatures around 180° C., and that the residues produced by the pyrolysis were platinum metals having high purity. Therefore, it is found that the compounds of Examples 1 and 2 are platinum complexes suitable for low temperature film formation.

On the other hand, as for the compound of Comparative Example, the temperature at which the weight decrease observed by TG ended was low (about 130° C.), but no residue remained after the end of the weight decrease. This result shows the following: while the compound of Comparative Example reached 130° C., pyrolysis did not proceed at all, and instead, all the sample used for the measurement evaporated. In other words, the result shows that the compound of Comparative Example is difficult to pyrolyze, and is not suitable for platinum thin film formation at low temperature.

Vaporization test: A vaporization test was performed with the compounds of Examples 1 and 2. The conditions for carrying out the test are as follows. The charge weight of the sample was 100 mg, the pressure was 80 Pa, and the heating temperature was 70° C. The proportion of the amount of decrease to the charge weight of the sample (taken as the rate of decrease) was calculated, and comparison was performed for the difficulty of the evaporation of the compounds. For the rate of decrease, values after 60 minutes and 90 minutes from the start of heating were calculated.

TABLE 2

|  | | Rate of decrease | |
| --- | --- | --- | --- |
|  | Heating temperature | After 60 minutes | After 90 minutes |
| Example 1 | 70° C. | 94 wt % | 100 wt % |
| Example 2 | 70° C. | 80 wt % | 100 wt % |

From the results of the rate of decrease after 60 minutes, it was found that the compound of Example 1 vaporized more easily than the compound of Example 2. The reason of this finding is considered that because the compound of Example 1 had a smaller molecular weight and a higher vapor pressure than the compound of Example 2, the amount of decrease due to evaporation of the compound of Example 1 increased. In addition, from the results of the rate of decrease after 90 minutes, it was found that as for the compounds of Examples 1 and 2, it was possible to vaporize all the charged samples without causing pyrolysis. From the above, as for the compounds of Examples 1 and 2, it was confirmed that at a platinum film formation stage (heating temperature: around 180° C.), the decomposition reaction proceeded rapidly; whereas at a vaporization stage (heating temperature: 70° C., pressure: 80 Pa), the decomposition reaction did not proceed and it was possible to stably vaporize the compounds.

Film formation test: A film formation test for a platinum thin film was performed by the CVD method with the compounds of Examples 1 and 2 and Comparative Example as raw materials. The film formation was carried out with a hot wall type film formation apparatus. In this apparatus, a raw material compound and a substrate on which a film was to be formed were placed in a glass pipe, the pipe was evacuated, and then, the outer wall of the pipe in the region where the raw material compound and the substrate were placed was heated with a heater for the vaporization and pyrolysis of the sample.

A platinum thin film was formed on a substrate (substrate size: 15 mm×15 mm) obtained by laminating a silicon dioxide film (film thickness 100 nm) on a silicon substrate with tetraethoxysilane (TEOS). The film formation conditions are as follows.
Film Formation Conditions for Platinum Thin Film
Sample heating temperature: 50° C.
Substrate heating temperature: 175, 200, 225, 250, 275, and 300° C.
Reaction gas: hydrogen
Flow rate: 10 sccm
Pressure: 60 Pa
Film formation time: 30 minutes The thickness of the formed platinum thin film was measured with a scanning electron microscope (SEM). In addition, the specific resistance of the platinum thin film was measured by the four probe method. The measurement results are shown in Table 3.

TABLE 3

|  | Example 1 | | Example 2 | | Comparative Example | |
| --- | --- | --- | --- | --- | --- | --- |
| Substrate temperature (° C.) | Film thickness (nm) | Specific resistance (µΩcm) | Film thickness (nm) | Specific resistance (µΩcm) | Film thickness (nm) | Specific resistance (µΩcm) |
| 300 | 34 | 53 | 37 | 51 | 21 | 132 |
| 275 | 31 | 57 | 35 | 55 | 18 | 154 |
| 250 | 28 | 66 | 32 | 56 | 14 | 207 |
| 200 | 18 | 83 | 27 | 51 | 9 | 256 |
| 175 | 26 | 91 | 26 | 74 | Film could not be formed | Impossible to measure |

From the results of the film formation test at 175° C., it was shown that the compounds of Examples 1 and 2 was capable of film formation at a lower temperature than the compound of Comparative Example. In addition, it was found that the platinum thin films formed with the compounds of Examples 1 and 2 showed smaller specific resistances than the platinum thin film formed with the compound of Comparative Example 1, and had small amounts of impurities. From the above results, it became clear that the compounds of Examples 1 and 2 are raw material compounds suitable for the production of a platinum thin film at low temperature.

INDUSTRIAL APPLICABILITY

The chemical vapor deposition raw material according to the present invention comprising an organoplatinum compound has the properties required of a CVD compound in good balance, has high vapor pressure, and is capable of film formation at low temperature. The present invention is also adaptable to the production of an electrode material having a steric structure.

What is claimed is:
1. A chemical vapor deposition raw material for producing a platinum thin film or a platinum compound thin film by a chemical vapor deposition method, wherein the chemical vapor deposition raw material comprises an organoplatinum compound having cyclooctadiene which is not substituted by an alkyl group, and alkyl anions coordinated to divalent plati- num, the organoplatinum compound being represented by the following formula: [Formula 1]

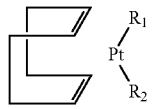

wherein R₁ is a methyl group and R₂ is a propyl group.

2. A chemical vapor deposition method for producing a platinum thin film or a platinum compound thin film, comprising the steps of vaporizing a raw material comprising an organoplatinum compound to form a raw material gas, and heating the raw material gas while introducing the raw material gas onto a substrate surface, wherein the chemical vapor deposition method comprises vaporizing the chemical vapor deposition raw material defined in claim 1 as the raw material.

3. A chemical vapor deposition raw material for producing a platinum thin film or a platinum compound thin film by a chemical vapor deposition method, wherein the chemical vapor deposition raw material comprises an organoplatinum compound having cyclooctadiene which is not substituted by an alkyl group, and alkyl anions coordinated to divalent platinum, the organoplatinum compound being represented by the following formula: [Formula 1]

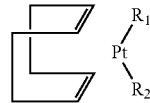

wherein R₁ is a propyl group and R₂ is an ethyl group.

4. A chemical vapor deposition method for producing a platinum thin film or a platinum compound thin film, comprising the steps of vaporizing a raw material comprising an organoplatinum compound to form a raw material gas, and heating the raw material gas while introducing the raw material gas onto a substrate surface, wherein the chemical vapor deposition method comprises vaporizing the chemical vapor deposition raw material defined in claim 3 as the raw material.

* * * * *